(12) United States Patent
Seguer Bonaventura et al.

(10) Patent No.: US 7,399,616 B2
(45) Date of Patent: Jul. 15, 2008

(54) ENZYMATIC SYNTHESIS OF N$^\alpha$-ACYL-L-ARGININE ESTERS

(75) Inventors: Joan Seguer Bonaventura, Barcelona (ES); Xavier Rocabayera Bonvila, Barcelona (ES)

(73) Assignee: Laboratorios Miret, S.A., Barcelona (ES)

( * ) Notice: Subject to any disclaimer, the term of this patent is extended or adjusted under 35 U.S.C. 154(b) by 326 days.

(21) Appl. No.: 10/501,941

(22) PCT Filed: Feb. 1, 2002

(86) PCT No.: PCT/EP02/01070

§ 371 (c)(1),
(2), (4) Date: May 23, 2005

(87) PCT Pub. No.: WO03/064669

PCT Pub. Date: Aug. 7, 2003

(65) Prior Publication Data

US 2006/0003427 A1 Jan. 5, 2006

(51) Int. Cl.
*C12P 13/00* (2006.01)
*C12P 13/02* (2006.01)
*C12P 13/04* (2006.01)
*C12P 13/20* (2006.01)

(52) U.S. Cl. .............. 435/106; 435/109; 435/128; 435/129

(58) Field of Classification Search .......... 435/106, 435/109, 129, 128
See application file for complete search history.

(56) References Cited

U.S. PATENT DOCUMENTS

| | | | | |
|---|---|---|---|---|
| 3,825,560 | A | 7/1974 | Saito et al. | 260/326.45 |
| 4,389,489 | A | 6/1983 | Preiss et al. | |
| 5,336,515 | A | 8/1994 | Murphy et al. | 426/573 |
| 5,681,802 | A | 10/1997 | Fujiwara et al. | 510/130 |
| 5,780,658 | A | 7/1998 | Martinez-Pardo et al. | 554/51 |
| 6,068,867 | A | 5/2000 | Nussinovitch et al. | 426/102 |
| 6,299,915 | B1 | 10/2001 | Nussinovitch et al. | 426/89 |
| 7,074,447 | B2 | 7/2006 | Bonaventura et al. | 426/321 |
| 2003/0049305 | A1 | 3/2003 | Von Rymon Lipinski et al. | 424/439 |
| 2004/0166082 | A1 | 8/2004 | Urgell-Beltran et al. | 434/70.21 |
| 2004/0175350 | A1 | 9/2004 | Urgell Beltran et al. | 424/70.27 |
| 2004/0265443 | A1 | 12/2004 | Beltran et al. | 426/321 |
| 2005/0175747 | A1 | 8/2005 | Seguer Bonaventura et al. | 426/323 |
| 2006/0003421 | A1 | 1/2006 | Markussen et al. | 435/69.1 |

FOREIGN PATENT DOCUMENTS

| | | |
|---|---|---|
| EP | 0 485 616 | 5/1992 |
| EP | 0 500 332 | 8/1992 |
| EP | 0 749 960 | 12/1996 |
| GB | 1 352 420 | 5/1974 |
| JP | 58039651 | 3/1983 |
| JP | 59164704 | 9/1984 |
| JP | 03291211 | 12/1991 |
| JP | 09188605 | 7/1997 |
| JP | 09255518 | 9/1997 |
| JP | 09286712 | 11/1997 |
| JP | 10045557 | 2/1998 |
| WO | 94/07377 | 4/1994 |
| WO | 94/19026 | 9/1994 |
| WO | 94/19027 | 9/1994 |
| WO | 96/21642 | 7/1996 |
| WO | PCT/US97/02156 | 2/1997 |
| WO | 01/49121 | 7/2001 |

OTHER PUBLICATIONS

*Enzymatic Synthesis of Arginine-Based Cationic Surfactants*; XP-001095996, 1999 John Wiley & Sons, Inc., pp. 333-343.

*Synthesis of glycero amino acid-based surfactants. Part 1. Enzymatic preparation* . . . XP-001105737, J. Chem Soc., Perkin Trans 1, 2001, pp. 2063-2070, The Royal Society of Chemistry 2001.

Chemical Abstracts Service, Columbus, Ohio, US; Garcia Dominguez, J. et al.: "Cationic Surfactants With Antimicrobial Activity" retrieved from STN Database Accession No. 107:79974, XP002196810, Abstract and ES 530 051 A (Consejo Superior De Investigaciones Cientificas, Spain) May 1, 1995.

(Continued)

*Primary Examiner*—Herbert J Lilling
(74) *Attorney, Agent, or Firm*—Renner, Otto, Boisselle & Sklar, LLP

(57) ABSTRACT

The invention relates to a process for preparing a Na-acyl-L-arginine ester, derived from fatty acids and esterified dibasic amino acids, according to the following formula (I), where: X— is Br—, Cl—, or HSO4— R1: is linear alkyl chain from an saturated fatty acid, or hydroxy-acid from 8 to 14 atoms of carbon bonded to the $\propto$-amino acid group through amidic bond. R2: is a linear or branched alkyl chain from 1 to 18 carbon atoms or aromatic. R3: is formula (II), where n can be from 0 to 4, from the appropriate organic acid and alcohol. The process is catalyzed by a hydrolase, more in particular a protease, the protease papain from <i> Carica papaya being highly suitable </i>. In order for the esterification reaction to run as wanted, the process is performed in a low-water-content organic medium. When the highly suitable papain from Carica papaya is used, a water activity of between 0.03 and 0.5 is selected.

22 Claims, 3 Drawing Sheets

OTHER PUBLICATIONS

Chemical Abstracts Service, Columbus, Ohio, US; Garcia Dominguez, J. J. et al.: "N.alpha.-Acyl-L-alkylaminoguanidinic Acids and Their Salts as Surfactants With Antimicrobial Action" retrieved from STN Database Accession No. 99:122920, XP002196912, Abstract and ES 512 643 A (Asociacion De Investigacion De Detergentes, Spain) Feb. 16, 1983.

Infante et al., Surface Active Molecules: Preparation and Properties of Long Chain Nα-Acyl-L-α-Amino-ω-Guanidine Alkyl Acid Derivatives; International Journal of Cosmetic Science 6, 1984, pp. 275-282.

Infante et al., A Comparative Study on Surface Active and Antimicrobial Properties of Some Nα-Lauroyl-Lα, ωDibasic Aminoacids Derivatives; Fette Seifen Anstrichmittel, No. 8, 1985, pp. 309-313.

Garcia Dominguez et al.; Monocapas de Algunos N-α-Acil Aminoacidos Antimicrobianos en Soluciones de NaCl; Anales de Quimica, vol. 82, 1986, pp. 413-418.

Infante et al.; The Influence of Steric Configuration of Some Nα-Lauroyl Amino-Acid Derivatives on Their Antimicrobial Activity; Fette Seifen Anstrichmittel, 88, No. 3, 1986, pp. 108-110.

Molinero et al.; Synthesis and Properties of Nα- Lauroyl-L-Argine Dipeptides From Collagen; JAOCS, vol. 65, No. 6, 1988, 4 pages.

Vinardell et al.; Comparative Ocular Test of Lipopeptidic Surfactants; International Journal of Cosmetic Science 12, 1990, pp. 13-20.

Kunieda et al.; Reversed Vesicles From Biocompatible Surfactants, Advanced Materials, No. 4, 1992, pp. 291-293.

Infante et al.; Sintesis y Propiedades de Tensioactivos Cationicos Derivados de Arginina; Anales de Quimica, vol. 88, 1992, pp. 542-547.

Fördedal et al.; Lipoamino Acid Association in the System Nα-Lauroyl-L-Arginine Methyl Ester—1-Pentanol—Water As Studied by Dielectric Spectroscopy; Colloids and Surfaces A: Physiochemical and Engineering Aspects, 79, 1993, pp. 81-88.

Infante et al., Non-Conventional Surfactants From Amino Acids and Glycolipids: Structure, Preparation and Properties; Colloids and Surfaces A: Physicochemical and Engineering Aspects 123-124, 1997, pp. 49-70.

Moran et al.; Chemical Structure/Property Relationship in Single-Chain Arginine Surfactants; Langmuir 2001, 17, pp. 5071-5075.

ENZYMATIC SYNTHESIS OF $N^\alpha$-ACYL-L-ARGININE ESTERS

This application is a 371 of PCT/EP02/01070 02/01/2002

FIELD OF THE INVENTION

This invention relates to a process for preparing $N^\alpha$-acyl-L-arginine esters with protective activity against microorganisms.

BACKGROUND OF THE INVENTION

Many antimicrobials are known to protect against specific and general bacteria. But, most of them display incompatibilities with the human skin and the mouth cavity mucous membranes, such as irritations and allergies, and are toxic to human beings as well.

On the other hand, it has been demonstrated that esters derived from lauric acid and L-arginine are biologically active substances, in particular, the ethyl ester of the laurylamide of the L-arginine monohydrochloride, hereafter referred to as LAE. LAE has the chemical structure of formula (1).

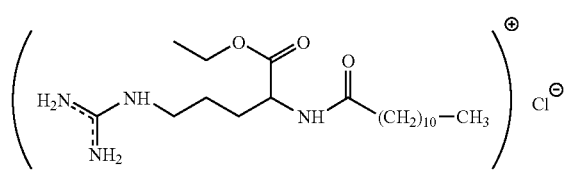

(1)

Biological studies carried out at different research centers showed LAE to act mainly over the external and cytoplasmatic membrane of the microorganisms and, also, into the cytoplasmatic medium, preventing their proliferation. Its action depends on the kind of microorganism and on the exposure time.

Besides, its metabolism in rats has been studied showing a fast absorption and metabolism into naturally-occurring amino acids and the fatty acid lauric acid, which are eventually excreted as carbon dioxide and urea. Toxicological studies have demonstrated that LAE is completely harmless to animals and humans.

These facts make LAE and related compounds very interesting as preservatives for food and cosmetic applications.

The preparation of these products by traditional chemical methods has been described in patent applications ES-515643, PCT/ES95/00027 and PCT/EP00/05072

SUMMARY

It was the object of the present invention to provide a new process to obtain such kind of compounds which is more efficient and selective than the traditional chemical methods, and therefore guarantees final products free of by-products and easy to isolate.

The existence of reversible metabolic degradation pathways for this kind of compounds represents an almost natural way to achieve LAE. Accordingly the process of the invention provides a process by enzymatic reversed reactions in organic solvents to obtain LAE and similar compounds from its corresponding readily available organic acid.

The synthesis of the invention relates to obtain $N^\alpha$-acyl-L-arginine esters according to the formula (2), where:

$X^-$: is $Br^-$, $Cl^-$, or $HSO_4^-$ $R_1$: is a linear alkyl chain from a saturated fatty acid or hydroxy-acid from 8 to 14 atoms of carbon bonded to the $\alpha$-amino acid group through an amide bond.

$R_2$: is a linear or branched alkyl chain from 1 to 18 carbon atoms or an aromatic group.

$R_3$: is:

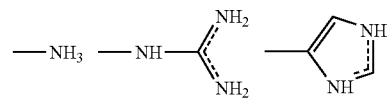

and n can be from 0 to 4; from the appropriate organic acid of formula (2) where $R_2$ is —H.

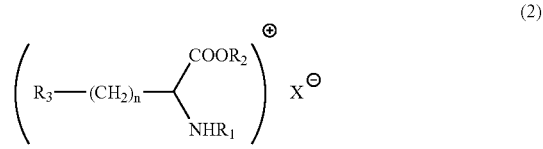

(2)

The most preferred compound of the above class of compounds is LAE.

BRIEF DESCRIPTION OF THE DRAWINGS

The invention is illustrated in the FIGS. 1 to 4.

DETAILED DESCRIPTION

Figure 1:
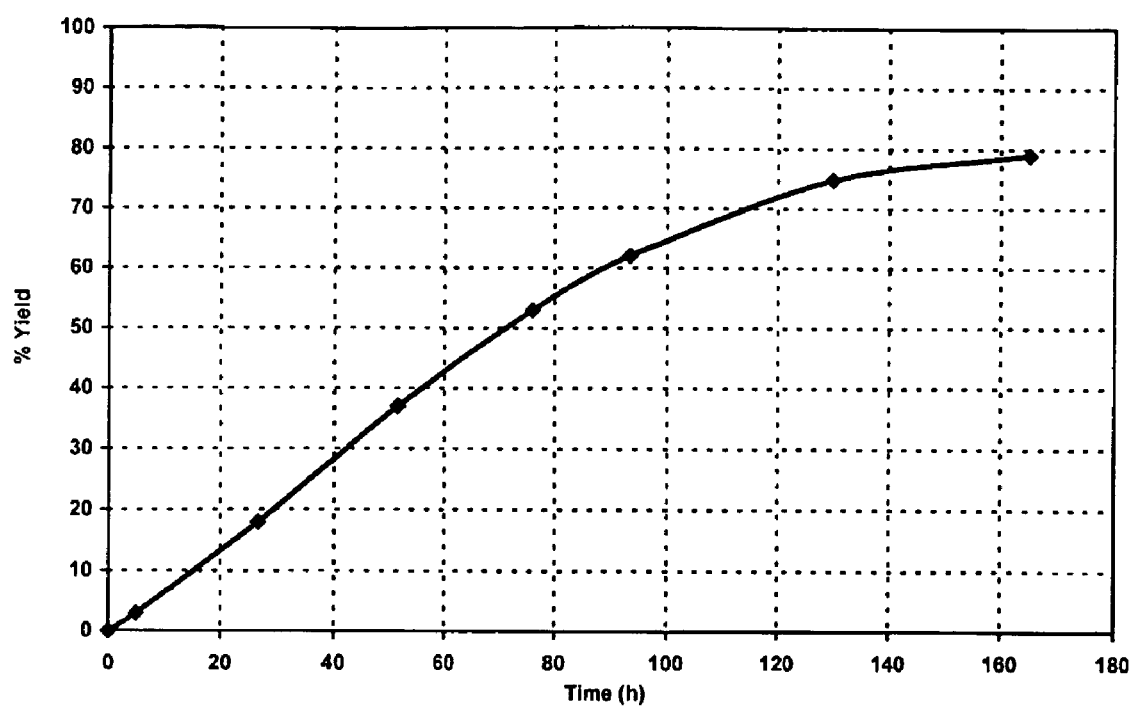
FIG. 1—Preparation of LAE, relationship yield-time.

The biocatalysis using enzymes in reverse hydrolysis reactions to obtain products with important industrial interest is described in many references.

This type of process may be performed in an aqueous medium with or without miscible or immiscible organic solvents, or in a organic solvent, or without any solvent at all. In the latter cases, the reaction naturally needs a minimum content of water for it to take place, as the enzyme otherwise loses its activity under such circumstance. The organic solvent usually contains less than 1% by weight of water, and is referred as low-water-content organic solvent.

Often, the water content is fixed at the beginning of the reaction and no control is performed along the process, however in reactions where water is consumed or produced, the water content becomes a critical value and has to be controlled by addition or elimination of water from the medium using salt hydrates or by other moisturizing or draining physical and/or chemical means.

The water content in an organic medium is frequently measured as water activity. The magnitude of the water activity represents the amount of non-linked water and depends on the water content but also on the nature of the solvent. The water activity is a thermodynamic parameter defined as the ratio of water vapors partial pressure above the solution in question to that above pure water of the same temperature and at the same total pressure, when the equilibrium between the liquid and the gas phase has been reached. Then the water activity is essentially equal to the fractional humidity in the gas phase. The water activity of pure water has a value of 1.

Besides the water content, the type of solvent, the pH employed and the temperature may affect kinetics, yield and/or by-products of the process, as all these factors have an influence on enzymatic activity.

As stated before, the catalytic reverse hydrolysis reaction is regularly performed under conditions of a low amount of water. On the other hand, enzymes are not soluble in organic solvents in spite of the presence of low amounts of water. This has been resolved by the adsorption onto solid supports. Adsorption may be achieved by adding the required amount of adsorbent to the reaction mixture or by providing the enzyme pre-adsorbed onto the support. If the pre-adsorption method is selected, then the enzyme has to be adsorbed in the correct level of ionization by using a buffer of the right pH at the adsorption process.

This invention relates to a new method for producing $N^\alpha$-acyl-L-arginine esters with microbiological activity derived from a fatty acid and L-arginine, according to formula (2), using the appropriate organic acid as starting material and enzymes in a low-water-content medium.

The method is based on the enzymatically promoted esterification of a $N^\alpha$-acyl-L-arginine acid, which has a linear alkyl chain from a saturated fatty acid or the hydroxy-acid with 8 to 14 carbon atoms bonded to the a-amino acid group through an amidic bond, with an alcohol consisting of a linear or branched chain from 1 to 18 carbon atoms or a phenylic group. This method has an elevated selectivity, is exempt from by-products, uses mild conditions and involves low toxicity reagents and solvents.

The enzyme may be obtained from a microbial source, or from plant or animal cells or tissues and may be present as a purified or a crude, relatively impure mixture of several different types of enzymes. The enzyme preparation may be in any form such as a free powder, or a lyophilized powder, or covalently linked or adsorbed onto a solid support. The enzyme may be used as a free dispersion in the reaction mixture or onto a solid support, made of materials such as polypropylenes, polyamides, diatomaceous earths, clays, zeolites, activated charcoals, carboxymethyl cellulose, cellulose esters and other substituted celluloses, ion exchange resins, porous glass beads, aluminum oxide, celite or silica gels. The most preferred embodiment for LAE synthesis is using a solid support, and among them, celite. It makes the enzyme easier to remove from the reaction medium by usual methods (e.g. filtration, centrifugation) and to recycle it for a new start of the process.

The enzymes which are suitable for the preparation of the compounds of formula (2) are lipases and esterases, since an ester bond is formed, and peptidases and proteases, as the main substrates are natural amino acid derivatives. Among them, the most appropriate enzymes are proteases, such as bromelaines, clostripain, collagenases, elastases, ficin, kallikreines, metallopeptidases, papain, chymopapain, pepsin, peptidases, proteinases, trypsines, chymotrypsines and carboxypeptidases, but the choice depends on the desired reaction product as the enzyme is chosen by its affinity and specific activity towards both substrates, the organic acid and the alcoholic precursors. So, for the enzymatic synthesis of LAE, clostripain, ficin, kallikreines, papain, chymopapain and trypsines are preferred, most preferably papain from *Carica papaya*.

The enzymes have been adsorbed onto the solid supports referred to previously in the invention according to usual techniques well-known for an expert in the matter, such as lyophilization or humectation, at the appropriate ionization level provided by means of a pH buffer solution. The working pH for papain from *Carica papaya* is from 3 to 10, preferably between 8 and 8.5.

As some alcohols are liquid, the reaction may proceed without the further addition of solvents. In all other cases, to disperse enzymatic systems and reagents or to solubilize them, a solvent ought to be used, such as any of sterically hindered alcohols, acetonitrile, cyclic ethers, chlorinated hydrocarbons, ketones, esters, ethers, aromatic hydrocarbons and aliphatic hydrocarbons. In general all these solvents are suitable, since they dissolve reagents and do not affect the enzymatic activity. The solvent composition is entirely dependent on the product which is desired.

Water or an appropriate buffer solution may also be added, to achieve the optimum water content for the enzymatic activity. So, at a high water content the hydrolysis process is important, but at a very low water content the hydrolysis process does not take place as the enzyme loses its activity. The water activity for papain from *Carica papaya* is between about 0.03 and 0.5, more preferable 0.05 to 0.2, most preferably 0.06 to 0.09.

To increase the yield of the reaction, in some cases, it is necessary to remove the water generated employing a chemical and/or physical draining method, in the form of water exchangers or hydrated salts or chemical dryers or molecular sieves or azeotropic distillation, but at such a rate that the water content in the reaction medium does not drop under the minimum water content for the enzymatic activity. These tools to remove the water may be inside the reaction vessel or in a separate location through which a certain amount of the reaction medium, filtered or not, is recirculated.

The temperature must be set over the freezing point of the solvent, e.g. −50° C. for hexane or −45° C. for acetonitrile or 11° C. for 1,4-dioxane, and below the solvent boiling point, e.g. 81° C. for acetonitrile or 101° C. for 1,4-dioxane or 76° C. for ethanol, more preferably between 15° C. and 50° C., most preferably between 25° C. an 40° C.

The reaction mixture may also contain further salts, solvents, desiccant agents or enzymes attached to different types of solid supports, which are different from the ones defined in the claims, to achieve the conversion of the mentioned L-arginine derivated acids to the respective esters.

The progress of the reaction is determined by conventional means such as chromatography (thin layer, gas, high performance liquid, and the like) or conductivity measurements. The reaction time may vary from 1 h to 7 days, depending on the reaction parameters such as temperature, pH, solvent, the enzyme, solid support, substrates, water activity and draining system. After the complete or desired conversion of the substrates to the final products has been achieved, the enzyme is removed by conventional means such as filtration or centrifugation. Reaction products of high chemical purity are then isolated by conventional means such as simple evaporation of the solvent, crystallization, precipitation, vacuum distillation and/or chromatographic methods.

EXAMPLES

The displayed examples are only a selection, and do not represent a restriction to the conditions, enzymes, solvents or draining systems of the synthetical method in other cases.

Example 1

$N^\alpha$-lauroyl L-arginine hydrochloride (obtained from lauroyl chloride and L-arginine in alkaline medium) is placed in a seal reaction vessel and dissolved in ethanol, containing 0.5% of boric acid/borate 0.1M pH=8.2 buffer, to obtain a $N^\alpha$-lauroyl L-arginine hydrochloride concentration of 32 g/L.

A catalyst is prepared which is composed of celite adsorbing 8% of the enzyme papain from *Carica papaya*. The adsorption is performed at pH=8.2 and the preparation comprises 8% by weight of the enzyme relative to the adsorbent and 4% of 1,4-dithio-DL-threitol by weight of adsorbent.

The catalytic system is added to the solution in a ratio of 6/1 referred to the amount of $N^\alpha$-lauroyl L-arginine hydrochloride.

The system is purged with argon.

The reaction is carried out at 25° C. for 7 days and while smoothly stirring. The process evolution is shown in FIG. 1.

After the completion of the reaction the reaction mixture is filtered to remove the adsorbed enzyme and the final product, LAE, is isolated by conventional means. The process yield is 79% of pure LAE.

Example 2

Figure 2:
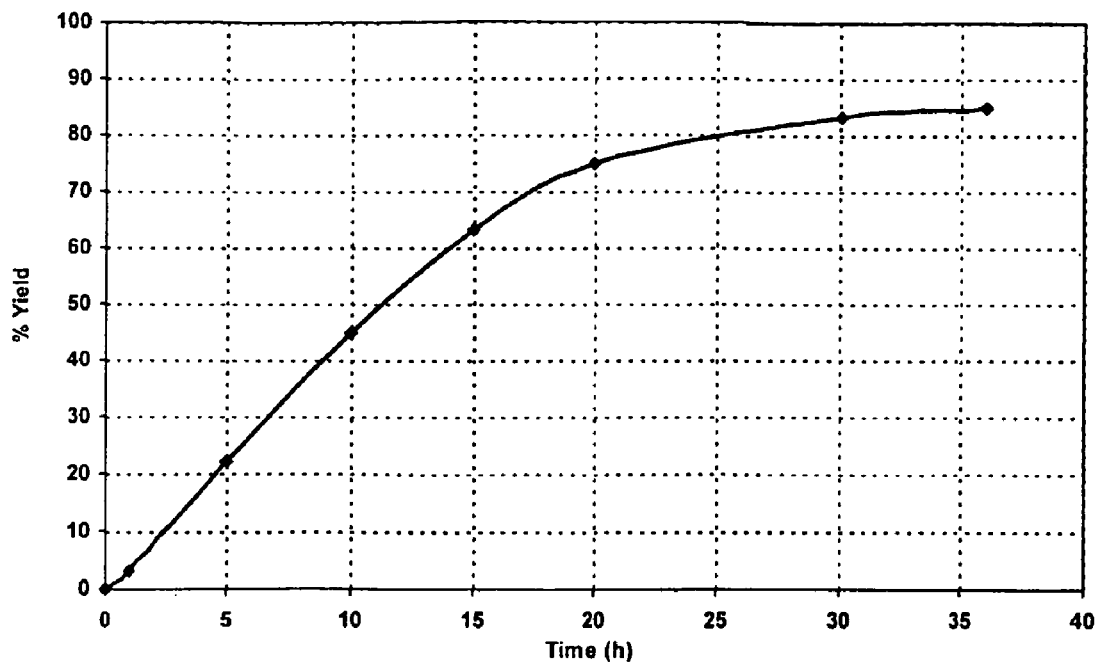
FIG. 2—Preparation of LAE, relationship yield-time.

The process is carried out under the same conditions as example 1, but using ethanol with 0.6% of buffer solution and at a reaction temperature of 40° C. for 36 hours. The process evolution is shown in FIG. 2.

The reaction mixture is filtered to remove the adsorbed enzyme and the final product, LAE, is isolated by conventional means. The process yield is 85% of pure LAE.

Example 3

This example demonstrates the use of a drying agent in an external device.

Figure 3:
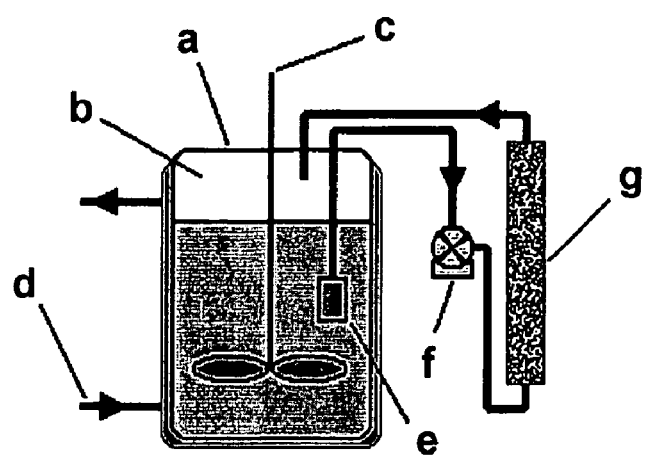
FIG. 3—Device for performing the process of the invention.

As FIG. 3 displays, the initial reaction mixture is placed in a closed vessel (a) under inert atmosphere (b) and equipped with:
- a stirring device (c);
- a jacket to keep the temperature at 35° C. by a warming or cooling fluid (d); and
- an outlet filter (e), through which a controlled flow of the filtered reaction mixture is taken by a peristaltic pump (f). This flow is passed through a molecular sieve drying column (g) in such a way that the water activity in the vessel is kept at about 0.06.

The initial reaction mixture has the same composition as example 2. The reaction is carried out for 24 hours at 35° C.

Figure 4:
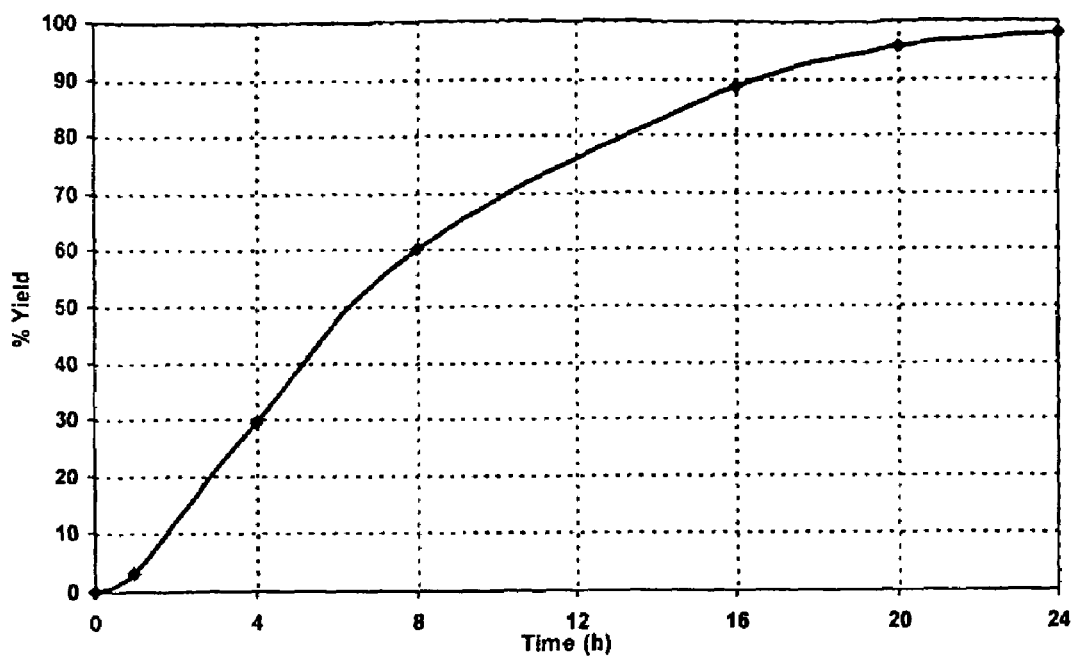
FIG. 4—Preparation of LAE, relationship yield-time.

The process evolution is shown in FIG. 4.

The reaction mixture is filtered to remove the adsorbed enzyme and final product, LAE, is isolated by conventional means. The process yield is 98% of pure LAE.

The invention claimed is:

1. A process for preparing a $N^\alpha$-acyl-L-arginine ester according to the following formula:

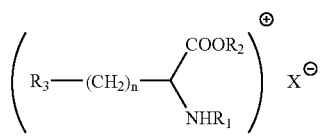

where:
$X^-$ is $Br^-$, $Cl^-$, or $HSO_4^-$
$R_1$ is a linear alkyl chain from a saturated fatty acid, or a hydroxy-acid, having from 8 to 14 atoms of carbon and being bonded to the α-amino acid group through amidic bond;
$R_2$ is a linear or branched alkyl chain from 1 to 18 carbon atoms or a phenylic group;
$R_3$ is:

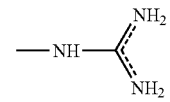

and n is 3, the process comprising reacting (i) a $N^\alpha$-acyl-L-arginine acid, as a cationic salt or acid salt, of the formula:

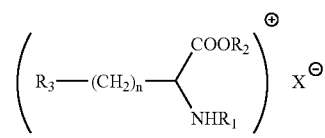

where $X^-$, $R_1$, and $R_3$ are as described above and $R_2$ is H, an organic cation, or an inorganic cation; and (ii) an alcohol with (a) a linear or branched alkyl chain from 1 to 18 carbon atoms or (b) a phenylic group, in the presence of (iii) a catalyst comprising a hydrolase, the reaction being carried out in a low-water-content organic medium.

2. The process as claimed in claim 1, wherein the $N^\alpha$-acyl-L-arginine ester is the ethyl ester of the laurylamide of L-arginine (LAE).

3. The process as claimed in claim 1, wherein the $N^\alpha$-acyl-L-arginine acid (i) is the $N^\alpha$-laurylamide of L-arginine.

4. The process as claimed in claim 1, wherein said hydrolase is a protease.

5. The process as claimed in claim 4, wherein said protease is papain from *Carica papaya*.

6. The process as claimed in claim 1, wherein the enzyme is adsorbed onto a solid support comprising at least one support chosen from polypropylenes, polyamides, diatomaceous earths, clays, zeolites, activated charcoals, substituted celluloses, ion exchange resins, insoluble polysaccharides, porous glass beads, aluminum oxide, celite, silica gels, and mixtures thereof.

7. The process as claimed in claim 6, wherein enzyme adsorption onto the solid substrate is carried out by lyophilization or humectation of a mixture of the solid support and a dispersion of the enzyme in an appropriate buffer solution.

8. The process as claimed in claim 1, wherein the low-water-content organic medium comprises at least one reaction solvent chosen from sterically hindered alcohols, acetonitrile, cyclic ethers, chlorinated hydrocarbons, ketones, esters, ethers, aromatic hydrocarbons, aliphatic hydrocarbons and mixtures thereof.

9. The process as claimed in claim 1, wherein the reaction is performed at a water activity between 0.02 and 0.1.

10. The process as claimed in claim 1, wherein the reaction is performed at a temperature between 20° C. and 45° C.

11. The process as claimed in claim 1, wherein the reaction is performed at a pH between 3 and 10.

12. The process as claimed in claim 1, wherein water generated in the reaction mixture is drained by a drying agent or a physical method, placed inside or outside of a vessel in which the reaction is performed.

13. A process for preparing a $N^\alpha$-acyl-L-arginine ester according to the following formula:

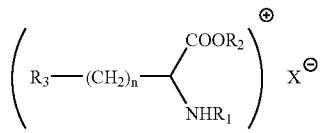

where:

$X^-$ is $Br^-$, $Cl^-$, or $HSO_4^-$ $R_1$ is a linear alkyl chain from a saturated fatty acid, or a hydroxy-acid, having from 8 to 14 atoms of carbon and being bonded to the α-amino acid group through amidic bond;

$R_2$ is a linear or branched alkyl chain from 1 to 18 carbon atoms or a phenylic group; and $R_3$ is:

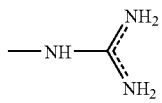

where n is 3, the process comprising reacting (i) $N^\alpha$-acyl-L-arginine acid, as a cationic salt or acid salt, of the formula:

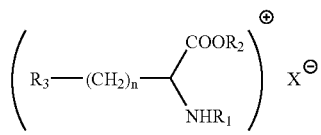

where $X^-$, $R_1$, and $R_3$ are as described above and $R_2$ is H, an organic cation or an inorganic cation; and (ii) an alcohol with (a) a linear or branched alkyl chain from 1 to 18 carbon atoms or (b) a phenylic group, in the presence of (iii) a catalyst comprising a protease, the reaction being carried out in a low-water-content organic medium, wherein the protease is adsorbed onto a solid support comprising at least one support chosen from polypropylenes, polyamides, diatomaceous earths, clays, zeolites, activated charcoals, substituted celluloses, ion exchange resins, insoluble polysaccharides, porous glass beads, aluminum oxide, celite, silica gels, and mixtures thereof.

14. The process as claimed in claim 13, wherein enzyme adsorption onto the solid support is carried out by lyophilization or humectation of a mixture of the solid support and a dispersion of the enzyme in an appropriate buffer solution.

15. The process as claimed in claim 13, wherein the low-water-content organic medium comprises at least one reaction solvent chosen from sterically hindered alcohols, acetonitrile, cyclic ethers, chlorinated hydrocarbons, ketones, esters, ethers, aromatic hydrocarbons, aliphatic hydrocarbons and mixtures thereof.

16. The process as claim in claim 13, wherein the $N^\alpha$-acyl-L-arginine ester is the ethyl ester of the laurylamide of L-arginine (LAE).

17. The process as claimed in claim 13, wherein said protease is papain from *Carica papaya*.

18. A process for preparing a $N^\alpha$-acyl-L-arginine ester according to the following formula:

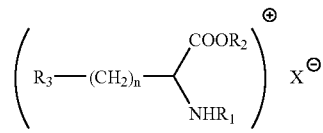

where:

$X^-$ is $Br^-$, $Cl^-$, or $HSO_4^-$ $R_1$ is a linear alkyl chain from a saturated fatty acid, or hydroxy-acid, having from 8 to 14 atoms of carbon and being bonded to the α-amino acid group through amidic bond;

$R_2$ is a linear or branched alkyl chain from 1 to 18 carbon atoms or aromatic a phenylic group; and $R_3$ is:

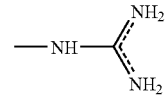

where n is 3, the process comprising reacting (i) $N^\alpha$-acyl-L-arginine acid, as a cationic salt or acid salt, of the formula:

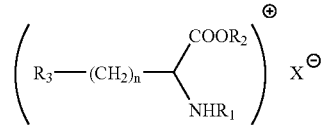

where $X^-$, $R_1$, and $R_3$ are as described above and $R_2$ is H, an organic cation or an inorganic cation; and (ii) an alcohol with (a) a linear or branched alkyl chain from 1 to 18 carbon atoms or (b) a phenylic group, in the presence of (iii) a catalyst comprising a papain from *Carica papaya*, the reaction being carried out in a low-water-content organic medium, wherein the papain is adsorbed onto a solid support comprising at least one support chosen from polypropylenes, polyamides, diatomaceous earths, clays, zeolites, activated charcoals, substituted celluloses, ion exchange resins, insoluble polysaccharides, porous glass beads, aluminum oxide, celite, silica gels, and mixtures thereof, and wherein the $N^\alpha$-acyl-L-arginine ester is the ethyl ester of the laurylamide of L-arginine (LAE).

19. The process as claimed in claim 18, wherein enzyme adsorption onto the solid support is carried out by lyophilization or humectation of a mixture of the solid support and a dispersion of the enzyme in an appropriate buffer solution.

20. The process according to claim 6, wherein the substituted cellulose is chosen from a carboxymethy cellulose, a cellulose ester, or combinations of two or more thereof.

21. The process according to claim 13, wherein the substituted cellulose is chosen from a carboxymethy cellulose, a cellulose ester, or combinations of two or more thereof.

22. The process according to claim 18, wherein the substituted cellulose is chosen from a carboxymethy cellulose, a cellulose ester, or combinations of two or more thereof.

* * * * *